(12) United States Patent
De Kock et al.

(10) Patent No.: US 8,527,067 B2
(45) Date of Patent: Sep. 3, 2013

(54) TAPERED DRUG-ELUTING COLLAR FOR A MEDICAL ELECTRICAL LEAD

(75) Inventors: Andrew De Kock, Andover, MN (US); Ronald W. Kunkel, Jim Falls, WI (US); Kimberly A. Morris, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 33 days.

(21) Appl. No.: 12/905,633

(22) Filed: Oct. 15, 2010

(65) Prior Publication Data

US 2011/0160831 A1 Jun. 30, 2011

Related U.S. Application Data

(60) Provisional application No. 61/291,204, filed on Dec. 30, 2009.

(51) Int. Cl.
*A61N 1/05* (2006.01)
(52) U.S. Cl.
USPC .......................... 607/120; 607/116; 607/121
(58) Field of Classification Search
USPC .......................................... 607/120–121, 116
See application file for complete search history.

(56) References Cited

U.S. PATENT DOCUMENTS

| | | | |
|---|---|---|---|
| 4,550,737 A | 11/1985 | Osypka | |
| 4,628,944 A | 12/1986 | MacGregor et al. | |
| 4,819,661 A | 4/1989 | Heil, Jr. et al. | |
| 4,819,662 A | 4/1989 | Heil, Jr. et al. | |
| 5,489,294 A | 2/1996 | McVenes et al. | |
| 5,522,872 A * | 6/1996 | Hoff | 607/119 |
| 5,531,780 A | 7/1996 | Vachon | |
| 5,545,206 A | 8/1996 | Carson | |
| 5,562,723 A | 10/1996 | Rugland et al. | |
| 5,662,697 A | 9/1997 | Li et al. | |
| 5,697,964 A | 12/1997 | Gates | |
| 5,713,945 A | 2/1998 | Fischer et al. | |
| 5,755,767 A | 5/1998 | Doan et al. | |
| 5,766,527 A | 6/1998 | Schildgen et al. | |
| 5,824,030 A | 10/1998 | Yang et al. | |
| 5,833,715 A | 11/1998 | Vachon et al. | |
| 5,853,652 A | 12/1998 | Schildgen et al. | |
| 5,902,329 A | 5/1999 | Hoffmann et al. | |
| 5,902,330 A * | 5/1999 | Ollivier et al. | 607/122 |

(Continued)

FOREIGN PATENT DOCUMENTS

| | | |
|---|---|---|
| WO | WO 01/45791 | 6/2001 |
| WO | 2005039691 | 5/2005 |
| WO | 2007059386 | 5/2007 |

OTHER PUBLICATIONS

International Search Report and Written Opinion issued in PCT/US2010/052876, mailed Mar. 2, 2011, 11 pages.

(Continued)

*Primary Examiner* — Carl H Layno
*Assistant Examiner* — Paula J Stice
(74) *Attorney, Agent, or Firm* — Faegre Baker Daniels LLP

(57) ABSTRACT

A medical electrical lead includes a tapered distal tip having a tapered drug-eluting component incorporated therein. The drug-eluting component can be an overmolded drug-eluting collar or a pre-molded drug eluting collar. The drug-eluting collar is disposed in a recess formed in the tapered distal tip and maintains the overall tapered profile of the distal tip.

12 Claims, 9 Drawing Sheets

(56) References Cited

U.S. PATENT DOCUMENTS

| | | |
|---|---|---|
| 5,931,864 A | 8/1999 | Chastain et al. |
| 5,987,746 A | 11/1999 | Williams |
| 5,991,668 A | 11/1999 | Leinders et al. |
| 6,038,482 A | 3/2000 | Vachon |
| 6,192,280 B1 * | 2/2001 | Sommer et al. ............... 607/122 |
| 6,253,110 B1 | 6/2001 | Brabec et al. |
| 6,298,272 B1 | 10/2001 | Peterfeso et al. |
| 6,304,786 B1 | 10/2001 | Heil, Jr. et al. |
| 6,360,129 B1 * | 3/2002 | Ley et al. ...................... 607/127 |
| 6,361,780 B1 | 3/2002 | Ley et al. |
| 6,363,286 B1 | 3/2002 | Zhu et al. |
| 6,363,287 B1 | 3/2002 | Brabec et al. |
| 6,385,491 B1 | 5/2002 | Lindemans et al. |
| 6,405,091 B1 * | 6/2002 | Vachon et al. ................ 607/120 |
| 6,459,937 B1 | 10/2002 | Morgan et al. |
| 6,549,812 B1 | 4/2003 | Smits |
| 6,716,444 B1 | 4/2004 | Castro et al. |
| 6,766,203 B2 | 7/2004 | Doan et al. |
| 6,889,092 B2 | 5/2005 | Zhu et al. |
| 7,013,181 B2 | 3/2006 | Westlund |
| 7,174,221 B1 | 2/2007 | Chen et al. |
| 7,184,839 B2 | 2/2007 | Clemens et al. |
| 7,239,923 B1 | 7/2007 | Liu et al. |
| 7,272,448 B1 | 9/2007 | Morgan et al. |
| 7,337,011 B2 | 2/2008 | Stokes et al. |
| 7,630,761 B2 * | 12/2009 | Salo et al. ........................ 607/3 |
| 7,953,499 B2 * | 5/2011 | Knapp et al. ................. 607/120 |
| 2003/0028231 A1 * | 2/2003 | Partridge et al. ............. 607/120 |
| 2003/0093136 A1 * | 5/2003 | Osypka et al. ................ 607/120 |
| 2003/0163171 A1 | 8/2003 | Kast et al. |
| 2004/0172117 A1 * | 9/2004 | Hill et al. ..................... 607/120 |
| 2004/0230272 A1 | 11/2004 | Cates et al. |
| 2004/0230273 A1 | 11/2004 | Cates et al. |
| 2004/0230274 A1 | 11/2004 | Heil et al. |
| 2005/0070985 A1 | 3/2005 | Allex et al. |
| 2005/0070988 A1 | 3/2005 | Kawula et al. |
| 2005/0245884 A1 | 11/2005 | Deininger |
| 2005/0267556 A1 * | 12/2005 | Shuros et al. ................. 607/120 |
| 2006/0041296 A1 * | 2/2006 | Bauer et al. ................... 607/122 |
| 2006/0134071 A1 | 6/2006 | Ross et al. |
| 2006/0134079 A1 | 6/2006 | Sih et al. |
| 2006/0136027 A1 | 6/2006 | Westlund et al. |
| 2006/0136028 A1 | 6/2006 | Ross et al. |
| 2006/0204717 A1 | 9/2006 | Deininger et al. |
| 2006/0235499 A1 * | 10/2006 | Heil et al. ..................... 607/127 |
| 2006/0282120 A1 | 12/2006 | Sih |
| 2007/0051531 A1 | 3/2007 | Borgaonkar |
| 2007/0191921 A1 * | 8/2007 | Zhu et al. ..................... 607/120 |
| 2007/0293922 A1 | 12/2007 | Soltis et al. |
| 2007/0299491 A1 | 12/2007 | Borgaonkar |
| 2008/0027526 A1 | 1/2008 | Zarembo |
| 2008/0057784 A1 * | 3/2008 | Zarembo et al. .............. 439/592 |
| 2008/0077217 A1 * | 3/2008 | Santamore et al. ........... 607/120 |
| 2009/0024197 A1 * | 1/2009 | Jensen ........................... 607/120 |
| 2009/0054961 A1 | 2/2009 | Borgaonkar et al. |
| 2009/0233491 A1 | 9/2009 | Barker et al. |
| 2009/0264943 A1 | 10/2009 | Barker |
| 2010/0004723 A1 | 1/2010 | Foster et al. |
| 2010/0125320 A1 * | 5/2010 | Polkinghorne et al. ....... 607/120 |

OTHER PUBLICATIONS

International Search Report and Written Opinion issued in PCT/US2009/062393, mailed Mar. 12, 2010, 16 pages.

* cited by examiner

TAPERED DRUG-ELUTING COLLAR FOR A MEDICAL ELECTRICAL LEAD

CROSS REFERENCE TO RELATED APPLICATIONS

This application claims the benefit under 35 U.S.C. §119 of U.S. Provisional Application No. 61/291,204, filed on Dec. 30, 2009, entitled "Tapered Drug-Eluting Collar for a Medical Electrical Lead," which is incorporated herein by reference in its entirety for all purposes.

TECHNICAL FIELD

The embodiments disclosed herein relate to body implantable medical devices, and more particularly, to medical electrical leads including an overmolded or pre-molded drug-eluting member.

BACKGROUND

Leads having electrodes implanted in or about the heart have been used to reverse life-threatening arrhythmia or to stimulate contraction of the heart. Electrical energy is applied to the heart via an electrode to return the heart to normal rhythm. Leads are usually positioned on or in the ventricle or the atrium and the lead terminals are attached to a pacemaker or defibrillator which is implanted subcutaneously.

One issue concerning, for example, pacemaker leads is the increase in stimulation threshold, both acute and chronic, caused by the interaction between the electrode and body tissue at the point of implant. Approaches to reducing the threshold include the incorporation of drug-eluting collars or plugs containing dexamethasone into the lead body. However, the size constraints imposed on the plug or collar matrix by the lead design limit the pharmacological therapy that can be provided to treat the complex nature of the natural healing process. Moreover, these devices many not adequately address many of the physiological processes involved in the healing response upon lead implantation.

SUMMARY

In Example 1, an implantable medical lead comprises a lead body including a proximal end adapted to be coupled to a pulse generator and a distal region including a distal tip having a tapered cross-sectional profile from a proximal end to a distal end of the distal tip. A recessed portion is formed in an outer surface of the tip. At least one conductor extends within the lead body from the proximal end to an electrode located on the distal region of the lead body, wherein the electrode operatively coupled to the at least one conductor. Additionally, the lead comprises a drug-eluting component disposed in the recessed portion formed in the distal tip, wherein the drug-eluting component has a tapered cross-sectional profile corresponding to the profile of the tip.

In Example 2, the implantable lead according to Example 1, wherein the tapered distal tip comprises silicone rubber.

In Example 3, the implantable lead according to any one of Examples 1-2, wherein the drug-eluting component comprises dexamethasone acetate and silicone rubber.

In Example 4, the implantable lead according to any one of Examples 1-3, wherein the tapered distal tip comprises silicone rubber and the drug-eluting component comprises dexamethasone and silicone rubber.

In Example 5, the implantable lead according to any one of Examples 1-4, wherein the drug-eluting component is an overmolded drug-eluting collar that encircles the tapered distal tip.

In Example 6, the implantable lead according to any one of Examples 1-5, wherein an outer surface of the drug-eluting component is flush with an outer surface of the tapered distal tip from the proximal end to the distal end of the tapered distal tip such that the tapered profile of the distal tip is maintained.

In Example 7, the implantable lead according to any one of Examples 1-6, wherein an outer surface of the drug-eluting component does not substantially protrude above an outer surface of the tapered distal tip, wherein a step tolerance between an outer surface of the drug-eluting collar and an outer surface of the distal tapered tip is less than about 0.005 inches.

In Example 8, the implantable lead according to any one of Examples 1-7, wherein the drug-eluting component is a pre-molded drug-eluting collar having a shape generally corresponding to the shape of the recessed portion.

In Example 9, the implantable lead according to any one of Examples 1-8, wherein the recessed portion includes one or more mechanical locking features adapted to receive a portion of the drug-eluting component.

In Example 10, the implantable lead according to any one of Examples 1-9, wherein a portion of the drug eluting component forms at least a portion of a distal tip end of the tapered distal tip such that the distal tip end is a drug-eluting tip end.

In Example 11, the implantable lead according to any one of Examples 1-9, wherein the recessed portion is formed in the tapered distal tip such that it is located between a proximal end and a distal end of the tapered distal tip.

In Example 12, the implantable lead according to any one of Examples 1-11, wherein the recessed portion is formed in the tapered distal tip such that it extends along a length of the distal tip from a proximal end to a distal end of the tapered distal tip.

In Example 13, an implantable medical lead comprises a lead body including a proximal end adapted to be coupled to a pulse generator and a distal region including a distal tip having a tapered cross-sectional profile from a proximal end to a distal end of the distal tip. A recessed portion is formed in an outer surface of the tip such that extends around an entire circumference of the tapered distal tip. At least one conductor extends within the lead body from the proximal end to an electrode located on the distal region of the lead body, wherein the electrode is operatively coupled to the at least one conductor. The lead also comprises a circumferential drug-eluting collar disposed in the recessed portion formed in the distal tip, wherein the drug-eluting collar has a tapered cross-sectional profile corresponding to the profile of the tip and extends around the entire circumference of the tapered distal tip.

In Example 14, the implantable lead according to Example 13, wherein the drug-eluting collar comprises dexamethasone acetate and silicone rubber.

In Example 15, the implantable lead according to any one of Examples 13-14, wherein the tapered distal tip comprises silicone rubber and the drug-eluting collar comprises dexamethasone and silicone rubber.

In Example 16, the implantable lead according to any one of Examples 13-15, wherein an outer surface of the drug-eluting collar is flush with an outer surface of the tapered distal tip from the proximal end to the distal end of the tapered distal tip such that the tapered profile of the distal tip is maintained.

In Example 17, the implantable lead according to any one of Examples 13-16, wherein an outer surface of the drug-eluting component does not substantially protrude above an outer surface of the tapered distal tip, wherein a step tolerance between an outer surface of the drug-eluting collar and an outer surface of the distal tapered tip is less than about 0.005 inches.

In Example 18, the implantable lead according to any one of Examples 13-17, wherein the drug-eluting collar is a pre-molded drug-eluting collar having a shape generally corresponding to the shape of the recessed portion.

In Example 19, the implantable lead according to any one of Examples 13-18, wherein the recessed portion includes one or more mechanical locking features adapted to receive a portion of the drug-eluting collar.

In Example 20, the implantable lead according to any one of Examples 13-18, wherein the drug-eluting collar is an overmolded drug-eluting collar that encircles the tapered distal tip.

In Example 21, the implantable lead according to any one of Examples 13-20, wherein a portion of the drug-eluting collar forms at least a portion of a distal tip end of the tapered distal tip such that the distal tip end is a drug-eluting tip end.

In Example 22, the implantable lead according to any one of Examples 13-21, wherein the recessed portion is formed in the tapered distal tip such that it is located between a proximal end and a distal end of the tapered distal tip.

In Example 23, the implantable lead according to any one of Examples 13-22, wherein the recessed portion is formed in the tapered distal tip such that it extends along a length of the distal tip from a proximal end to a distal end of the tapered distal tip.

In Example 24, a method of assembling a medical electrical lead including a drug-eluting component comprises the steps of: forming a tapered distal tip region of a medical electrical lead body comprising a recessed portion; and overmolding a drug-eluting component within the recessed portion of the tapered distal tip region to form a tapered drug-eluting component having an outer surface that is flush with an outer surface of the tapered distal tip region and wherein the tapered profile of the tapered distal region is maintained.

In Example 25, the method according to Example 24, wherein the step of overmolding the drug-eluting component comprises positioning the lead body in a mold and injecting a polymer matrix including a bioactive agent into the mold.

In Example 26, the method according to any one of Examples 24-25, wherein the drug eluting component is overmolded from a polymer matrix material comprising silicone rubber and dexamethasone acetate.

In Example 27, a method of assembling a medical electrical lead including a drug-eluting component comprises the steps of: forming a tapered distal tip region of a medical electrical lead body comprising a recessed portion; and bonding a pre-molded drug-eluting component to the recessed portion of the tapered distal tip region such that an outer surface of the drug-eluting component does not substantially protrude beyond an outer surface of the tapered distal tip region and the tapered profile of the tapered distal region is maintained.

In Example 28, the method according to Example 27, wherein the step of bonding comprises applying a layer of a medical adhesive to the recessed portion to adhesively bond the pre-molded drug-eluting component to the recessed portion.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Various embodiments disclosed herein relate to a medical electrical lead having an overmolded or pre-molded drug-eluting component. The leads according to the various embodiments of the present invention are suitable for sensing intrinsic electrical activity and/or applying therapeutic electrical stimuli to a patient. Exemplary applications include, without limitation, cardiac rhythm management (CRM) systems and neurostimulation systems. For example, in exemplary CRM systems utilizing pacemakers, implantable cardiac defibrillators, and/or cardiac resynchronization therapy (CRT) devices, the medical electrical leads according to embodiments of the invention can be endocardial leads configured to be partially implanted within one or more chambers of the heart so as to sense electrical activity of the heart and apply a therapeutic electrical stimulus to the cardiac tissue within the heart. Additionally, the leads formed according to embodiments of the present invention may be particularly suitable for placement in a coronary vein adjacent to the left side of the heart so as to facilitate bi-ventricular pacing in a CRT or CRT-D system. Still additionally, leads formed according to embodiments of the present invention may be configured to be secured to an exterior surface of the heart (i.e., as epicardial leads).

Figure 1:
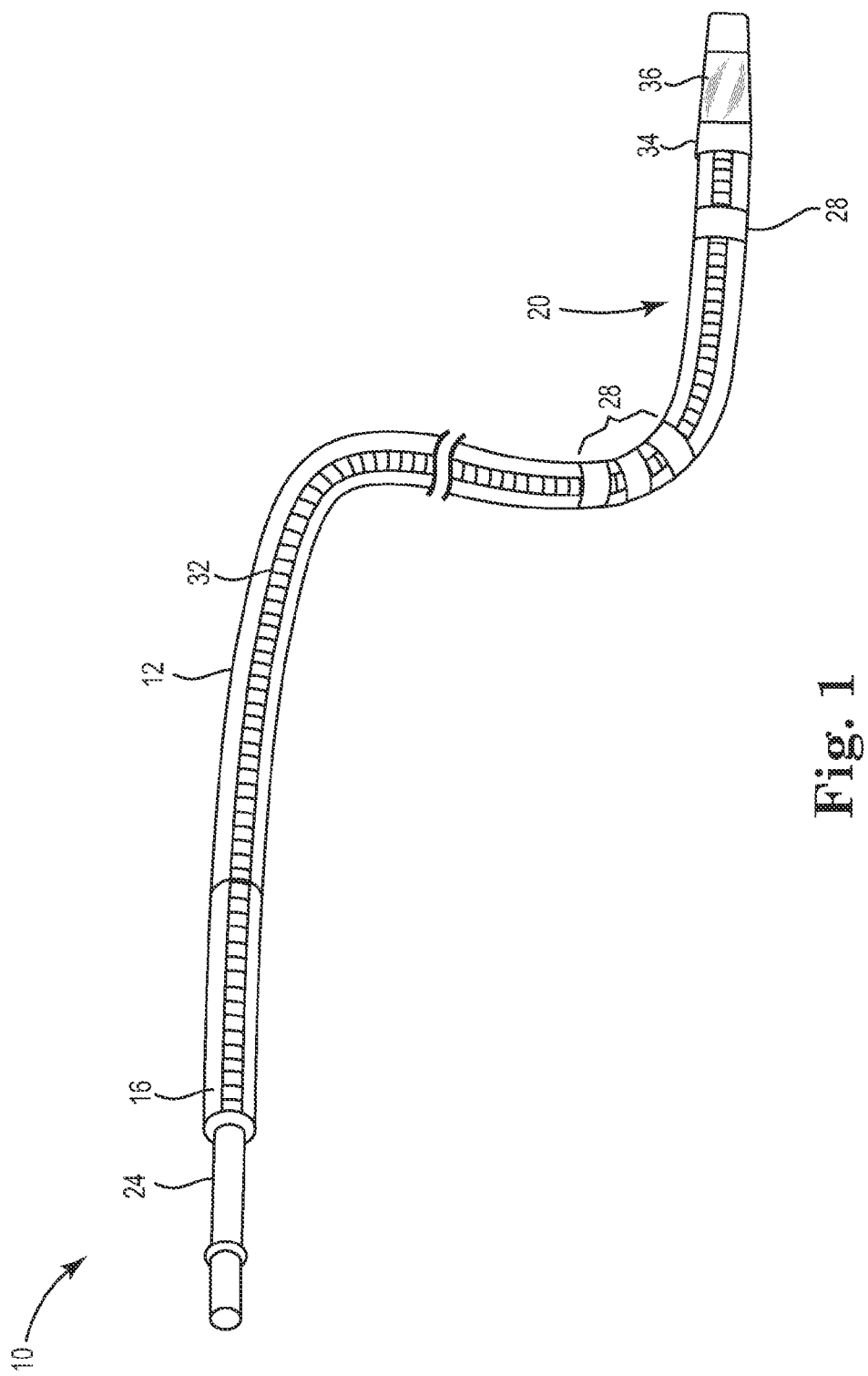
FIG. 1 is a schematic cross-sectional view of a cardiac lead according to an embodiment of the invention.

FIG. 1 is a partial cross-sectional view of a medical electrical lead 10, according to various embodiments of the present invention. According to some embodiments, the medical electrical lead 10 can be configured for implantation within a patient's heart. The medical electrical lead 10 includes an elongated, polymeric lead body 12 extending from a proximal end 16 to a distal end 20. The polymeric lead body can be fabricated from a variety of materials including polyurethane, silicone rubber and the like. The proximal end 16 is configured to be operatively connected to a pulse generator via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors are employed, the lead can include a combination of coiled and cable conductors. When a coiled conductor is employed, according to some embodiments, the conductor can have either a co-radial or a co-axial configuration.

The lead body 12 is flexible, but substantially non-compressible along its length, and typically has a circular cross-section although other cross-sectional shapes such as, for example, elliptical may be employed. According to one embodiment of the present invention, an outer diameter of the lead body 12 ranges from about 2 to about 15 French.

In some embodiments, as shown in FIG. 1, the lead body 12 includes a tapered distal tip 34. The tapered distal tip 34 can be manufactured from the same or different polymeric material than the rest of the lead body 12. In one embodiment, the tapered distal tip is fabricated from silicone rubber to maintain the flexibility needed to facilitate implantation of the lead 10 at a location within the patient's heart. Additionally, the tapered shape of the tip 34 facilitates deeper penetration of the distal end 20 of the lead 10 into the heart vessel during the implantation procedure.

The medical electrical lead 10 can be unipolar, bipolar, or multi-polar depending upon the type of therapy to be delivered. In embodiments of the present invention employing multiple electrodes 28 and multiple conductors 32, each conductor 32 is adapted to be connected to an individual electrode 28 in a one-to-one manner allowing each electrode 28 to be individually addressable. Additionally, the lead body 12 can include one or more lumens adapted to receive a guiding element such as a guidewire or a stylet for delivery of the lead 10 to a target location within a patient's heart.

The electrodes 28 can have any electrode configuration as is known in the art. According to one embodiment of the present invention, at least one electrode can be a ring or partial ring electrode. According to another embodiment, at least one electrode 28 is a shocking coil. According to yet another embodiment of the present invention, at least one electrode 28 includes an exposed electrode portion and an insulated electrode portion. In some embodiments, a combination of electrode configurations can be used. The electrodes 28 can be coated with or formed from platinum, stainless steel, MP35N, a platinum-iridium alloy, or another similar conductive material.

According to various embodiments, the lead body 12 can include one or more fixation members for securing and stabilizing the lead body 12 including the one or more electrodes 28 at a target site within a patient's body. The fixation member(s) can be active or passive. An exemplary active fixation member includes a screw-in fixation member. Examples of passive fixation include pre-formed distal portions of the lead body 12 adapted to bear against the vessel walls and/or expandable tines provided at the distal end of the lead body 12.

Additionally, the medical electrical lead 10 also includes one or more drug-eluting components 36. The drug-eluting component 36 can be overmolded or pre-molded and can be located anywhere along the length of the lead body 12. When the lead 10 is implanted, the drug-eluting component 36 releases a bioactive agent into the body environment that suppresses the inflammatory response and/or other unwanted biological processes associated with implantation and the presence of the foreign object. In addition, the bioactive agent may also reduce the growth of non-excitable, connective tissue and/or prevent myocyte cell function impairment and/or necrosis around or near the electrode (e.g., the capsule). According to one embodiment, the drug-eluting component 36 is a collar.

Figure 2:
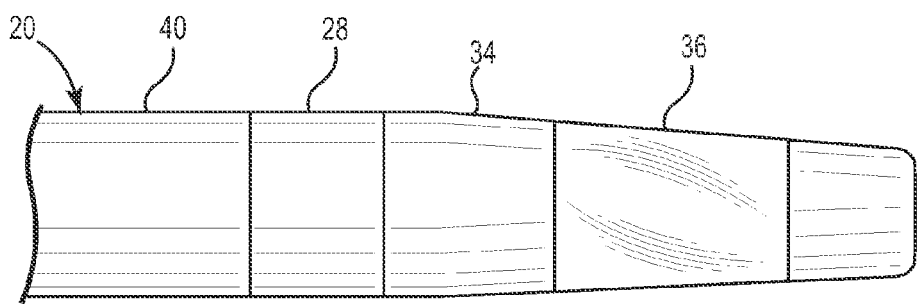
FIG. 2. is a schematic view of a distal tip region of the cardiac lead shown in FIG. 1 according to an embodiment of the present invention.

FIG. 2 is a schematic view of a distal tip region 40 of a lead body 12 including a drug-eluting component 36 according to various embodiments of the present invention. The drug-eluting component 36 is incorporated into the tapered distal tip 34 of the lead body 12 and is located distal to the distal most electrode 28. In some embodiments, the drug-eluting component 36 extends at least partially around an outer circumference of the tapered distal tip 34. In other embodiments, as shown in FIG. 2, the drug-eluting component 36 is a drug-eluting collar 36 that encircles an outer circumference of the tapered distal tip 34. In one embodiment, the drug-eluting collar 36 is an overmolded drug-eluting collar 36. In another embodiment, the drug-eluting collar 36 is a pre-molded drug-eluting collar 36.

Figure 3A:
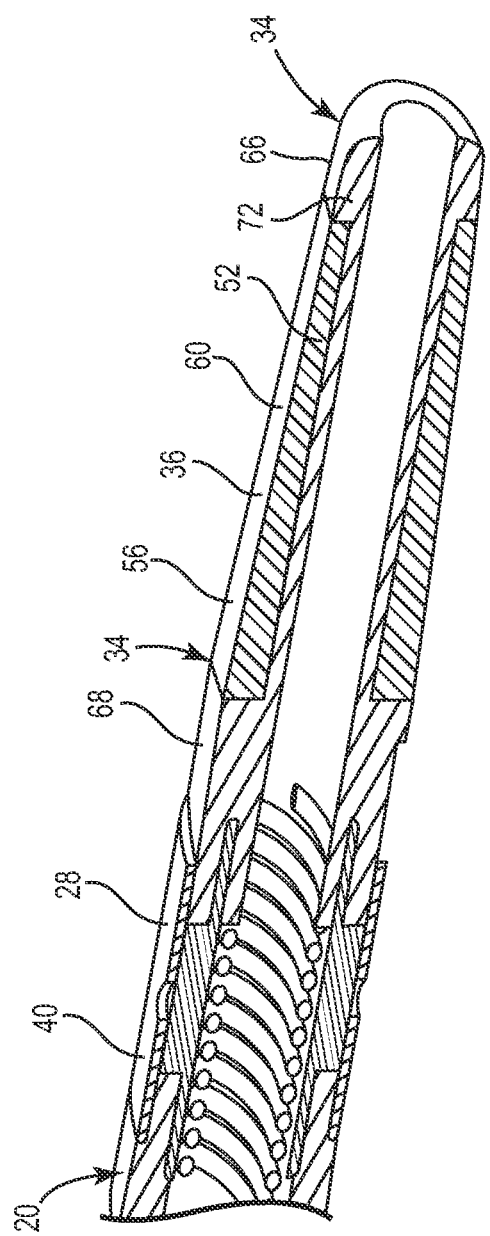
FIG. 3A is a cross-sectional view of a portion of a lead body with a drug-eluting collar, according to another embodiment of the present invention.

FIG. 3A is a cross-sectional view of the distal tip region 40 of the lead body 12 including a drug-eluting collar 36 is incorporated into the tapered distal tip 34. When incorporated into the tapered distal tip 34, the drug-eluting collar 36 should maintain the flexibility of the tapered distal tip 34 for implantation of the lead 10. The drug-eluting collar 36 is disposed in a recessed portion 52 formed in the tapered distal tip 34. Like the tapered distal tip 34, the drug-eluting collar 36 also has a tapered profile or shape 56 such that it corresponds to and maintains the overall tapered profile of the tip. For example, in one embodiment, the outer surface 60 of the tapered drug-eluting collar 36 is flush with an outer surface 66 of the tapered distal tip 34 from a proximal end 68 to the distal end 72 of the tip 34 such that it maintains the overall tapered profile of the tip. In another embodiment, the outer surface 60 of the tapered drug-eluting collar 36 does not substantially protrude above the outer surface 66 of the tapered distal tip 34. In this embodiment the step tolerance between the outer surface 60 of the drug-eluting collar 36 and the outer surface 66 of the distal tapered tip 34 is less than about 0.005 inches. In some embodiments, the step tolerance may range from about 0.003 inches to about 0.005 inches.

Figure 3B:
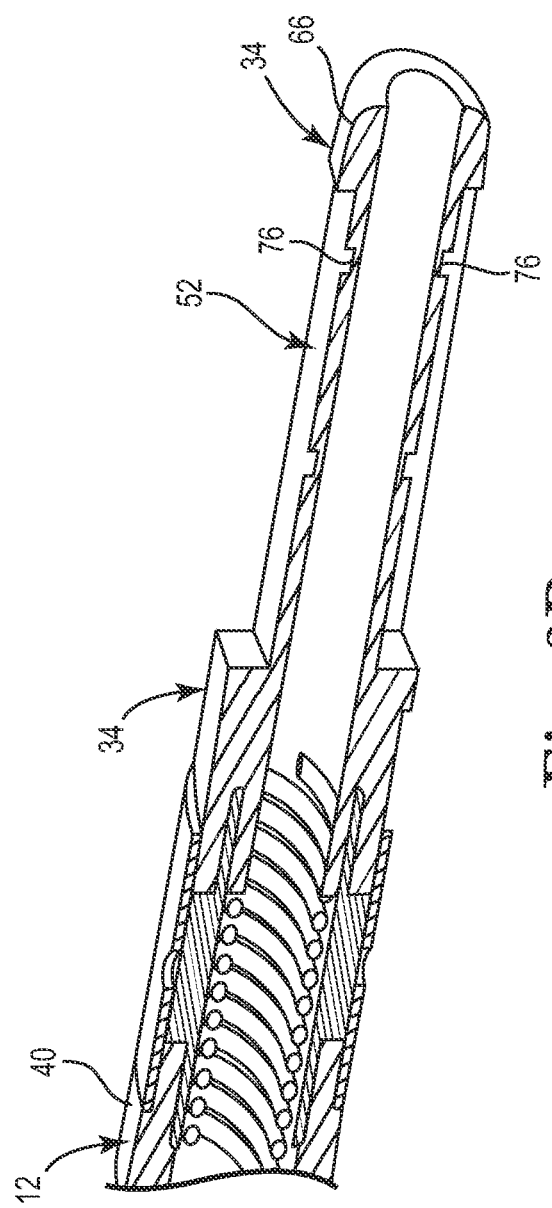
FIG. 3B is a cross-sectional view of the lead body portion shown in FIG. 3A excluding the drug-eluting collar.

FIG. 3B is a cross-sectional view of the distal tip 34 of the lead body 12 excluding the drug-eluting collar 36. As shown in FIG. 3B, the distal tip 34 includes a recessed portion 52 configured to receive the drug-eluting collar 36. In one embodiment the recessed portion 52 is formed in the outer surface 66 of the tapered distal tip 34 such that it extends at least partially around the outer circumference of the tapered distal tip 34. In some embodiments, such as depicted in FIG. 3B, the recessed portion 52 is formed in the outer surface 66 of the tapered distal tip 34 such that it extends around an entire circumference of the tapered distal tip 34. Additionally, in some embodiments, the recessed portion 52 is formed in the outer surface 66 of the tapered distal tip 34 such that it is located between a proximal end 68 and a distal end 72 of the tapered distal tip 34. In other embodiments, the recessed portion 52 is formed in the outer surface 66 of the tapered distal tip 34 such that it extends along a length of the tapered distal tip 34 from a proximal end 68 to a distal end 72 of the tapered distal tip 34.

According to various embodiments, the recessed portion 52 is formed in the outer surface 66 of the tapered distal tip 34 such that it also has a generally tapered cross-sectional profile from extending from a proximal end 68 to a distal end 72 of the tapered distal tip 34. In one embodiment, the recessed portion 52 is located between the proximal end 68 and distal end 72 of the tapered distal tip 34. In another embodiment, the recessed portion 52 is formed in an outer surface 66 of the tapered distal tip 34 such that it is a wedge-like recess having a tapered profile extending from a proximal end 68 through the distal end 72 of the tapered distal tip 34.

As will be described in greater detail below, the drug-eluting collar 36 can be overmolded into the recessed portion 52 such that the shape of the overmolded drug-eluting collar 36 generally corresponds to the shape of the recessed portion 52. In one embodiment the recessed portion 52 can include one or more mechanical locking features 76 that are adapted to receive a portion of the overmolded drug-eluting collar 36 therein. The mechanical locking features 76 promote adhesion between the overmolded drug-eluting collar 36 and the recessed portion 52 by providing an additional bonding mechanism between the overmolded drug-eluting collar 36 and the recessed portion 52.

In another embodiment, the drug-eluting collar 36 is a pre-molded drug-eluting collar 36. The pre-molded drug-eluting collar 36 has a shape generally corresponding to the shape of the recessed portion 52 such that the pre-molded drug-eluting collar 36 mates with the recessed portion and does not substantially protrude above the outer surface 66 of the distal tip 34. The pre-molded drug-eluting collar 36 is bonded to the recessed portion 52 using a medical adhesive or other suitable bonding method known to those of skill in the art. In one embodiment, the pre-molded drug-eluting collar 36 may include one or more mechanical locking features that are designed to mate with a corresponding mechanical locking feature provided in the recessed portion 52. The mechanical locking features provide an additional mechanism for bonding the pre-molded drug-eluting collar to the recessed portion.

Figure 4:
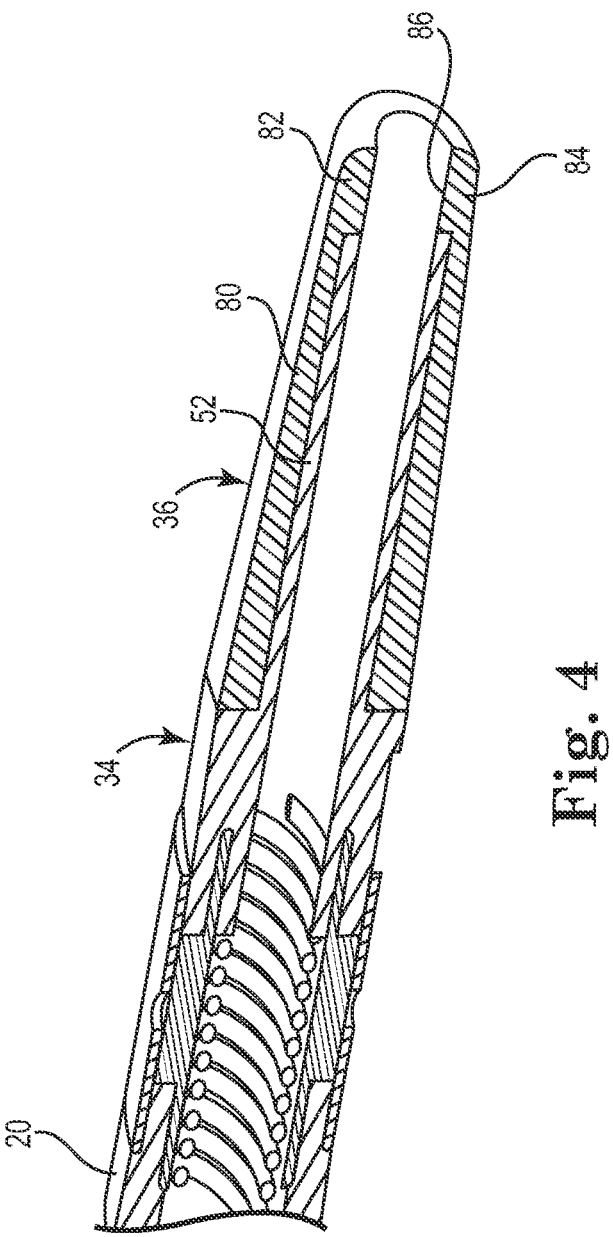
FIG. 4 is a cross-sectional view of a portion of a lead body according to yet another embodiment of the present invention.

FIG. 4 is a cross-sectional view of the distal tip region 40 of the lead body 12 according to yet another embodiment of the present invention. As depicted in FIG. 4, a drug-eluting collar 80 is disposed in the recessed portion 52 formed in the tapered distal tip 34 of the lead body 12. The drug-eluting collar 80 has a tapered profile that corresponds to and maintains the overall tapered profile of the distal tip 34 of the lead body 12. Additionally, the drug-eluting collar 80 forms at least a portion of the distal tip end 82 of the lead body 12 such that the distal tip end 82 is a drug-eluting tip end 82. The portion of the drug-eluting collar 80 forming the tip end 82 extends from an outer surface 84 of the tip end 82 to an inner surface 86. The drug-eluting collar 80 including the tip end 82 can be either an overmolded drug-eluting collar 80 or a pre-molded drug-eluting collar 80.

It is generally understood that the tapered drug-eluting collars 36, 80, described above, can be modified as necessary or desired to be used with a variety of electrode/end ring configurations.

In accordance with one embodiment, the drug-eluting components 36, 80 described above have an exposed surface area that ranges in size from about 0.1 $cm^2$ to about 5 $cm^2$. Alternatively, the surface area ranges from about 0.03 $cm^2$ to about 0.3 $cm^2$.

According to one implementation, the drug-eluting component 36 or 80 is a combination of a polymer and an agent, which can be any drug or bioactive agent. For example, in one embodiment the polymer is liquid silicone rubber ("LSR") and the drug is dexamethasone acetate ("DXA"). DXA is an anti-inflammatory agent. Alternatively, the drug-eluting component 36 or 80 can have more than one bioactive agent.

The polymer, according to one embodiment, can include, but is not limited to, one or more of the following polymers: Solef® (Solef® 21508 polymer); polyvinylidene-hexafluoropropylene or poly(VF2-co-HFP) from Solvay, Brussels, Belgium; acetoxy cure, Room-Temperature-Vulcanizing (RTV) silicone elastomers; UV curable silicone; UV curable polymer; platinum catalyzed addition cure liquid silicone rubber; styrene isobutylene styrene (SIBS); peroxide cure silicone rubber; Nafion; silicone (including LSR), polymers based on the structural unit $R_2SiO$, where R is an organic group; medical adhesives; cyanoacrylates; Rehau 1511; ethylene vinyl alcohol (E/VAL; a thermoplastic polymer); polyethylene glycol (PEG); polyvinyl alcohol; polyvinyl propylene; hyaluronic acid; polyacrylamides; polycaprolactone, polylactide (PLA); polyglycolide (PGA); poly(lactide-co-glycolide) (PLGA); polyurethane; polymethylmethacrylates; polyethylene; polyvinylpyrrolidone; polyacrylic acid; poly(2-hydroxyethyl methacrylate); pHEMA polyacrylamide; polyethylene-co-vinyl acetate; polyanhydrides; polyorthoesters; polyimides; polyamides; polyanhydrides; polyetherketones; polyaryletherketones; polysiloxane urethanes; polyisobutylene copolymers; and copolymers and combinations thereof.

The bioactive agent can be any drug or bioactive agent which can serve as a useful therapeutic, prophylactic, or even diagnostic agent when released into the patient. Exemplary bioactive agents include, but are not limited to, the following: an anti-inflammatory; anti-proliferative; anti-arrhythmic; anti-migratory; anti-neoplastic; antibiotic; anti-restenotic; anti-coagulation; anti-infectives; anti-oxidants; anti-macrophagic agents (e.g., bisphosphonates); anti-clotting (e.g., heparin, coumadin, aspirin); anti-thrombogenic; immunosuppressive agents; an agent that promotes healing, such as a steroid (e.g., a glucocorticosteroid) and/or re-endothelialization; and combinations thereof.

More specifically, the one or more bioactive agents may include, but are not limited to, the following: paclitaxel; clobetasol proprionate; rapamycin; sirolimus; everolimus; tacrolimus; actinomycin-D; dexamethasone (e.g., dexamethasone, dexamethasone sodium phosphate or dexamethasone acetate); betamethasone; mometasone furoate; vitamin E; mycophenolic acid; cyclosporins; beclomethasone (e.g., beclomethasone dipropionate anhydrous); their derivatives, analogs, salts; and combinations thereof. Additionally, the one or more bioactive agents may include bisphosphonates. Bisphosphonates inhibit macrophage-like action, thereby limiting the local inflammatory response. According to yet other embodiments, the one or more bioactive agents may include non-steroidal anti-inflammatory agents such as aspirin, ibuprofen, acetaminophen, and COX inhibitors (e.g., celecoxib and/or diclofenac).

According to another embodiment, the one or more bioactive agents can include one or more diagnostic agents such as, for example, radio opaque materials such as barium sulfate, platinum powder, tungsten powder, zirconium dioxide, bismuth trioxide and/or bismuth subcarbonate. In one embodiment, the one or more diagnostic agents can be combined with one or more other bioactive agents. Alternatively, the one or more diagnostic agents need not be combined with any other agents.

The bioactive agent can be present in the drug-eluting component in any effective amount. An "effective amount" generally means an amount which provides the desired local or systemic effect. For example, an effective dose is an amount sufficient to affect a beneficial or desired clinical result. The precise determination of what would be considered an effective dose may be based on factors individual to each patient, including their size and age. In one embodiment, the therapeutic agent is present in a concentration ranging from about 1 µg/cm² to about 20 mg/cm². Alternatively, the agent is present in a concentration ranging from about 1 to about 20 mg/cm². In a further alternative, the agent may also be present at a concentration of higher than about 20 mg/cm².

The drug-eluting component can be formed such that it includes an effective drug to polymer ratio (D:P). The drug to polymer ratio (D:P) can be selected for specific release properties. The release rate of the drug from the component can be manipulated through selection of an appropriate drug to polymer ratio to achieve the desired drug release profile. The drug to polymer ratio in the component can be selected such that the drug release profile is immediate, short term, or sustained release. A drug-eluting component having an immediate release profile releases the drug content within minutes to about an hour after implantation. A drug-eluting component having a short term release profile more slowly liberates the content within days to weeks following implantation. Finally, a drug-eluting component having a sustained release profile releases the content very slowly, with full release requiring months to years. According to one embodiment, the drug to polymer ratio in the drug-eluting component can be selected such that it ranges from 1:50 to 1:1. According to another embodiment, the drug to polymer ratio in the drug-eluting component can be selected such that it ranges from 1:10 to 1:1. Typically, a drug-eluting component including a higher drug to polymer ratio will have a faster drug release profile. Additionally, the selection of the polymer included in the component can also affect the release rate of the drug.

In one embodiment, the drug-eluting component 36 or 80 is manufactured by mixing the polymer and the agent together. For example, one implementation calls for mixing the polymer(s) and the bioactive agent(s) together to produce the drug-eluting component. In one embodiment in which the polymer is LSR and the bioactive agent is DXA, the LSR is provided in liquid form and the DXA is provided in powder form.

Regardless of the specific components, the polymer and bioactive agent are typically combined and mixed together in a mixer. In one embodiment, the mixer is a static mixer. It is understood in the art that a static mixer is a device for blending or mixing at least two materials. The mixer has mixer elements disposed within a cylindrical or squared housing. In use, the materials to be mixed are delivered into and through the mixer. As the materials flow through the mixer, the non-moving mixer elements disposed within the cylinder cause the materials to blend or mix together. The extent of mixing is impacted by the mixer length, the inner diameter of the housing, the number of mixer elements, the mixer element design, and flow rate.

In one aspect, a static mixer can allow for a more homogenous component mixture than can typically be achieved by other types of mixers. Such homogeneity results in sturdier molded components with less variation, thereby allowing for components with thinner walls and more uniform drug distribution, thereby leading to more repeatable drug release.

Alternatively, the mixer can be a centrifugal mixer. In a further alternative, a liquid injection system is provided (similar to the system disclosed below) that includes a mixer for mixing the components. According to a further implementation, the mixing can be accomplished using continuous line mixing, which is also known as meter mixing. The mixing can also be accomplished in another embodiment using acoustic mixing. In yet another alternative, any known mixer can be used.

In one embodiment, the quantity of the components that are mixed together can range from about 1 g to about 100 kg. Alternatively, in one implementation using a centrifugal mixer, the components range in amount from about 10 g to about 1 kg. In a further alternative using a static or continuous mixer, the components range in amount from about 1 kg to about 100 kg.

In one implementation in which a centrifugal or other type of rotating mixer is used, the components are mixed together at a rate ranging from about 700 rpm to about 3500 rpm for a period ranging from about 10 seconds to about 10 minutes. Alternatively, the components are mixed together by a mixer running at a rate ranging from about 1700 rpm to about 2500 rpm. In another alternative, the components are mixed together for a period ranging from about 30 seconds to about 2 minutes.

In a further alternative, the components are mixed together in a process that utilizes both types of mixers. That is, according to one embodiment, the components are first mixed in a centrifugal mixer and then subsequently mixed in a static mixer. Alternatively, the components can be first mixed in a static mixer and then subsequently mixed in a centrifugal mixer.

In accordance with one implementation, the components are mixed in two stages. In the first stage, a first portion of the polymer and a first portion of the bioactive agent are added to the mixer and mixed together. In the subsequent second stage, a second portion of the polymer and a second portion of the bioactive agent are added and mixed together. In one embodiment, a centrifugal mixer is used, and the materials of the first stage are mixed together from about 10 seconds to about 10 minutes, or alternatively from about 30 seconds to about 2 minutes. Subsequently, the materials of the second stage are mixed together from about 10 seconds to about 10 minutes, or alternatively from about 30 seconds to about 2 minutes. In one embodiment, the two portions of the mixture are then further mixed in a static mixer.

Alternatively, the components are mixed in two stages in a static mixer. In a further alternative, the mixture is then further mixed in a centrifugal mixer.

Figure 5A:
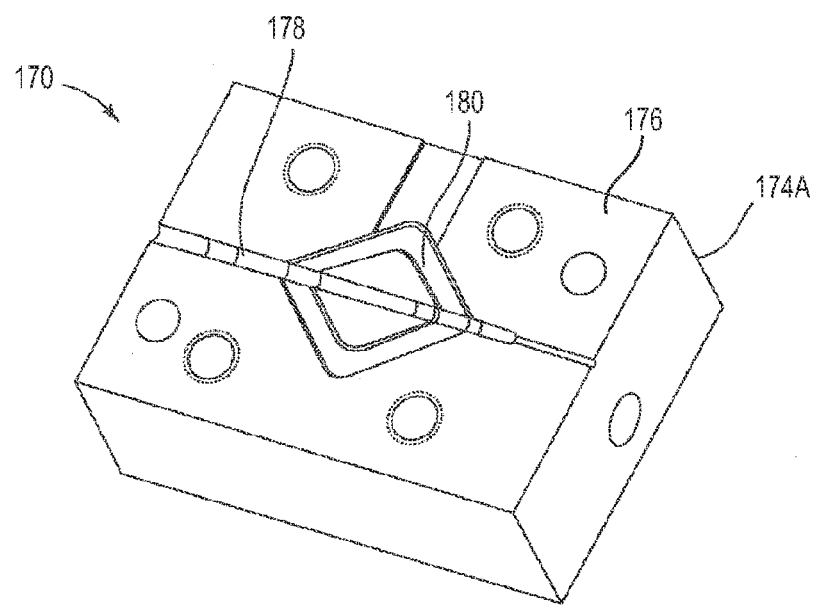
FIG. 5A is a perspective view of the bottom half of a mold, according to one embodiment.
Figure 5B:
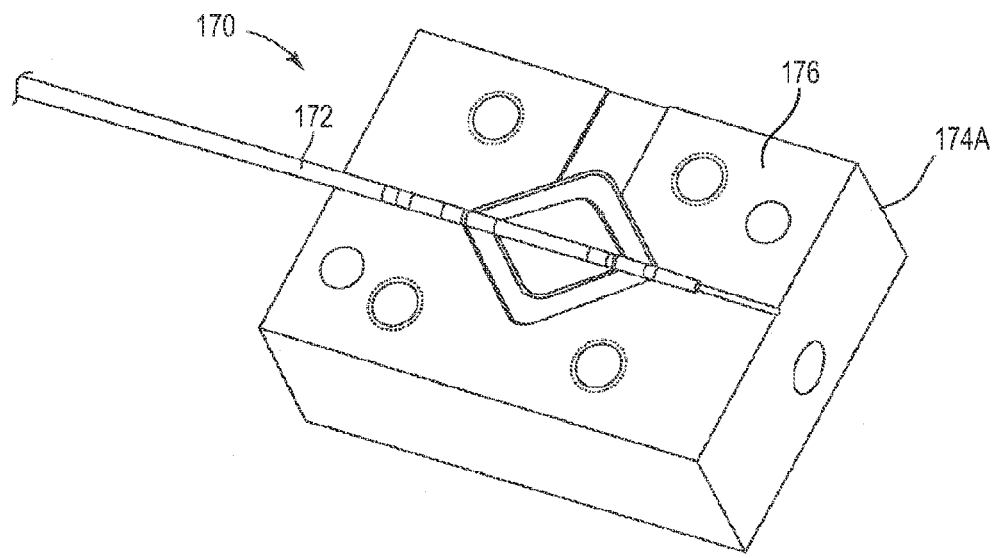
FIG. 5B is a perspective view of the bottom half of the mold of FIG. 5A and a lead body, according to one embodiment.
Figure 5C:
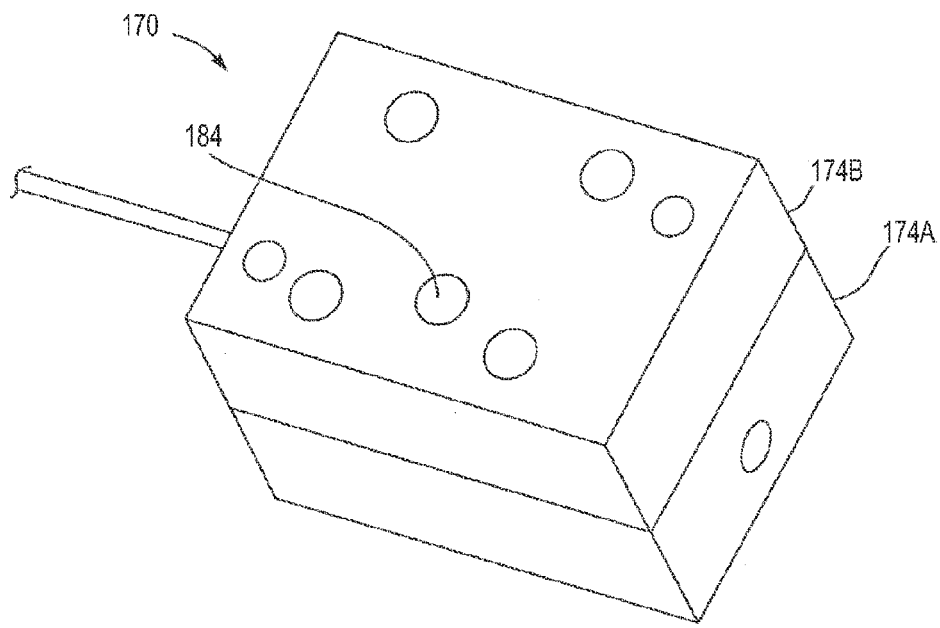
FIG. 5C is a perspective view of the top half combined with the bottom half of the mold of FIG. 5A and a lead body, according to one embodiment.
Figure 5D:
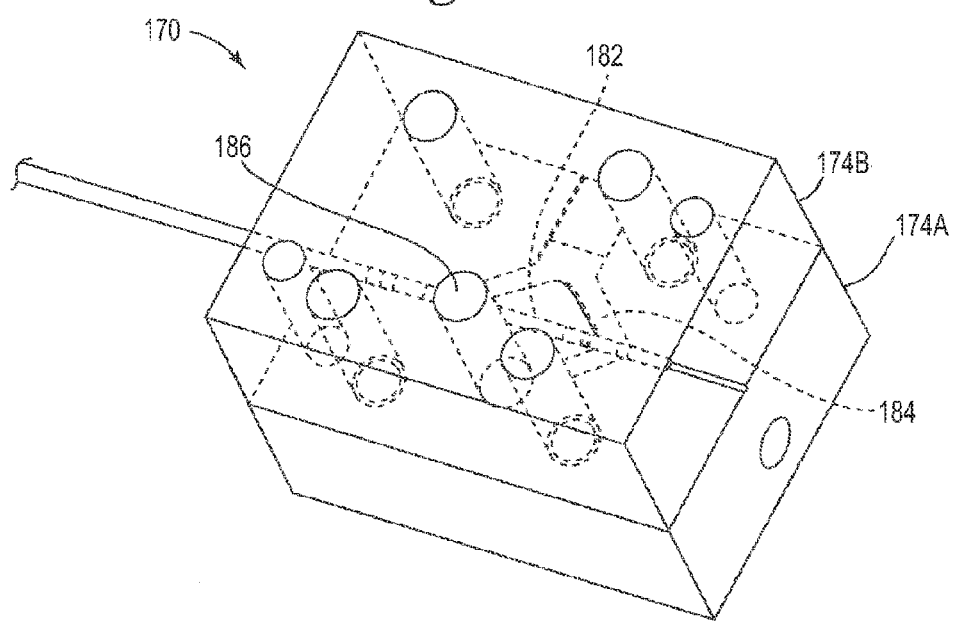
FIG. 5D is a perspective view of the top half combined with the bottom half of the mold of FIG. 5A and a lead body, according to one embodiment.
Figure 5E:
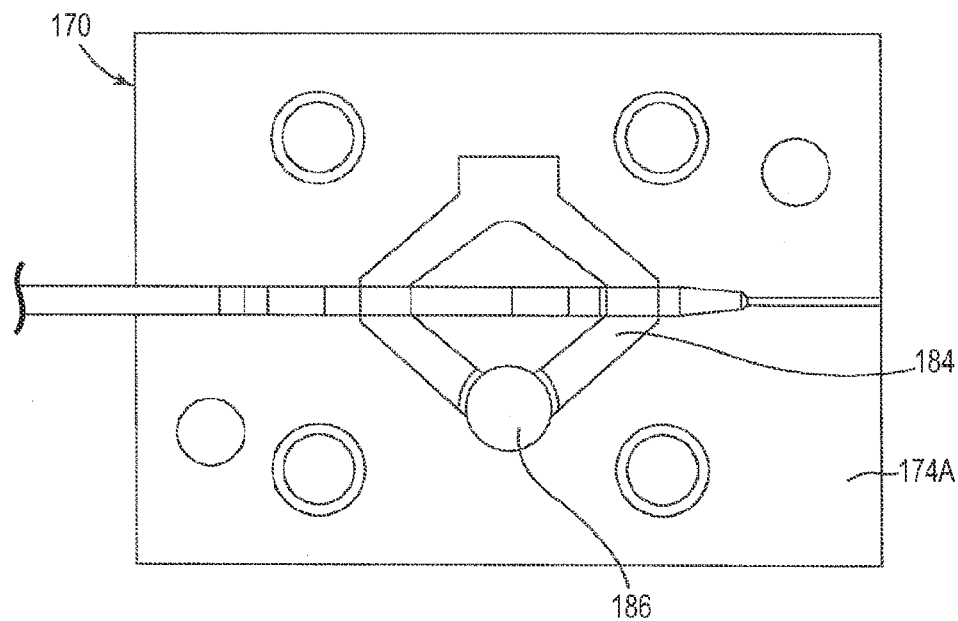
FIG. 5E is a top view of the bottom half of the mold of FIG. 5A, according to one embodiment.
Figure 5F:
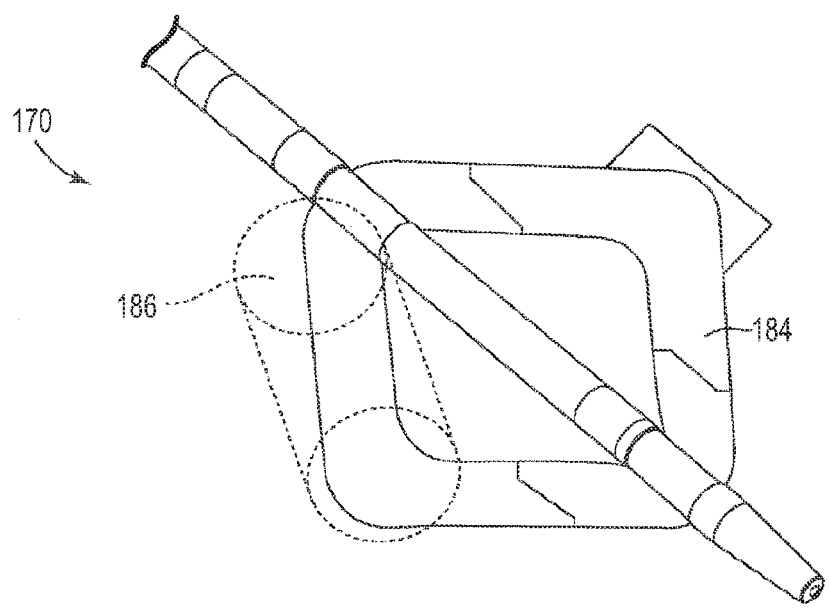
FIG. 5F is an expanded perspective view of the bottom half of the mold of FIG. 5A, according to one embodiment.

When the mixing is complete, according to one embodiment, the liquid mixture is added to a mold containing a lead body, such as the exemplary mold 170 and lead body 172 as depicted in FIGS. 5A-5F. In this embodiment, as best shown in FIGS. 5C and 5D, the mold 170 has two halves: a first (or lower) half 174A and a second (or upper) half 174B.

FIG. 5A depicts the lower half 174A of the mold 170 in its uncoupled configuration in which the halves 174A, 174B are not coupled, according to one implementation. The lower half 174A defines recesses and holes along its contact face 176. The recesses in the lower half 174A are a lead receiving recess 178 and an overmolding recess 180. It is understood that the contact face (not shown) of the upper half 174B has identical recesses that, when the two halves are coupled together as shown in FIGS. 5C and 5D, match up the recesses defined in the lower half 174A to define the lead receiving cavity 182 into which the lead is positioned and the overmolding cavity 184 into which the mixture described above is added to be overmolded onto the lead.

It is noted that in FIG. 5D, in which the mold is depicted in the coupled configuration, the lower half 174A is depicted as a solid or opaque body, while the upper half 174B is schematically depicted as a transparent body in outlined form to allow depiction of the interior portions of the mold 170. It is understood, however, that an actual mold would typically be opaque.

Referring now to FIG. 5D, the lead receiving cavity 182 is a cavity in which the lead body 172 or a component thereof can be positioned as shown, while the overmolding cavity 184 is the cavity into which the liquid mixture can be injected or otherwise disposed to form the drug-eluting component over the lead body 172. It is understood that the shape of the lead receiving cavity 182 can be defined as desired to receive any of a variety of configurations of lead bodies to which one or more drug-eluting components are desired to be added. Similarly, it is understood that the shape of the overmolding cavity 184 can be defined as desired to produce any of a variety of configurations of drug-eluting components. For example, as described above, the resulting component can take the form of one or more plugs, strips, spirals, dots, tines, or any other known shapes or configurations that could be used to deliver a bioactive agent to the patient.

A mold such as the mold 170 depicted in FIGS. 5A-5F can be used in the following fashion, according to one embodiment. As shown in FIG. 5B, the lead body 172 to which the drug-eluting component is to be added is positioned in the first half 174A of the mold 170, and more specifically is positioned in the lead receiving cavity 178 as best shown in FIG. 5A. Alternatively, the lead body 172 can be positioned in the lead receiving cavity (not shown) of the second half 174B.

Once the lead body 172 is positioned as desired, the first half 174A and second half 174B are coupled together as best shown in FIGS. 5C and 5D such that the lead receiving recess 178 of the first half 174A is in communication with and matched up with the lead receiving recess (not shown) of the second half 174B to create the lead receiving cavity 182. Once the two halves 174A, 174B are successfully coupled, the mixture of precursor components (already mixed as described above) can be injected into the mold 170. In one embodiment as shown in FIGS. 5C-5F, the upper half 174B has a channel 186 in communication with the overmolding cavity 184 through which the precursor components can be injected into the cavity 184. As can be seen in these figures, the components are injected or otherwise placed through the channel 186 and into the overmolding cavity 184. As the components fill up the cavity 184, they surround and adhere to the lead body 172 or a component thereof at the two portions of the body 172 that are positioned in the cavity 184. It is understood that the lead body 172 or component thereof can be polymeric or metallic or any other material of a component of a lead body 172. Alternatively, the precursor components can be injected into the overmolding cavity 184 by any known mechanism or method.

According to one embodiment, the process can involve two or more overmolding steps. That is, the process can include a first overmolding step that overmolds a first set of one or more components onto a lead body and a second overmolding step that overmolds a second set of one or more components that are positioned directly over the first set of components or in some overlapping configuration. Further, the process can include more than two overmolding steps, resulting in multiple components or components having multiple layers of overmolded material. In any embodiment in which two or more layers are added to create a layered component or multiple components, it is understood that one or more of the layers may contain a bioactive agent, while one or more of the layers may not. In a further embodiment, one or more of the layers could be a component that promotes adhesion, while one or more of the layers could control release of the bioactive agent in one or more of the other layers.

In a further implementation, it is further understood that the process described above can also be used to overmold one or more collars onto two or more lead bodies simultaneously. That is, the mold can be configured to define more than one lead body receiving cavity into which more than one lead body would be positioned. In this embodiment, the overmolding cavity is a single cavity that is in fluid communication with each of the lead body receiving cavities. Alternatively, the mold can have a separate overmolding cavity for each of the lead body receiving cavities.

Figure 6:
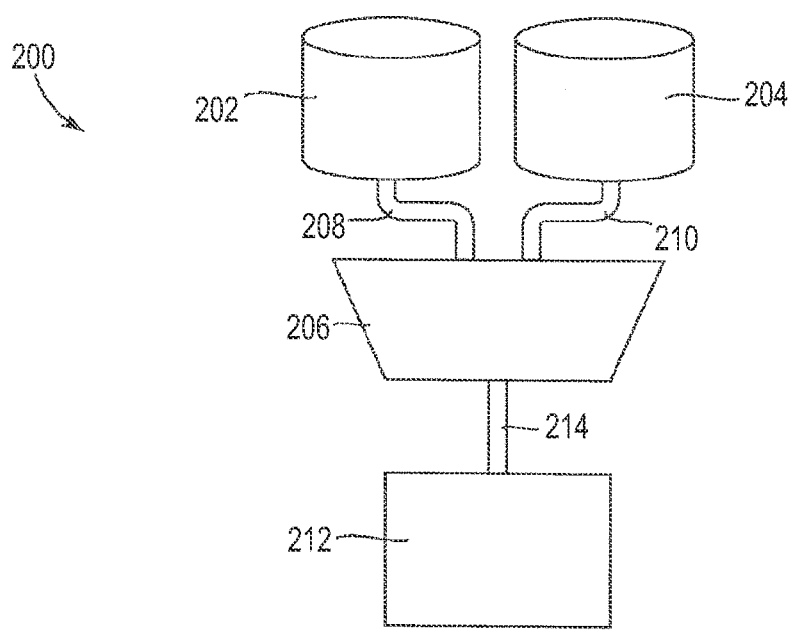
FIG. 6 is a schematic view of a liquid injection system, according to one embodiment.

In one embodiment as best depicted schematically in FIG. 6, a liquid injection system 200 is used to inject the mixture into the mold (not shown). In this embodiment, the liquid injection system 200 has a polymer container 202 and a bioactive agent container 204, which are in communication with a mixer 206 via lines 208, 210, respectively. Alternatively, the first container 202 receives a first polymer and bioactive agent and the second container 204 receives a second polymer and bioactive agent. Further, the mixer 206 is in communication with a press 212 via a line 214.

Alternatively, the system 200 can have a single container (instead of the separate polymer and bioactive agent containers) that receives the mixture of the polymer and bioactive agent. In such an embodiment, the components are mixed together prior to addition of the mixture to the container. For example, if there are two polymer components and a bioactive agent, the three components are mixed together prior to being added to the container.

In a further alternative, the system 200 can have three containers, including the first polymer component container, a second polymer component container, and the bioactive agent container. In this embodiment, the two polymer components are maintained in separate containers to prevent the polymer components from combining and beginning to cure. In one implementation having three containers, the first and second polymer containers can be positioned such that the two polymers are combined and mixed in a mixer and then the bioactive agent is added to that mixture and all three components are mixed together in a second mixer.

In use, a polymer is placed in the polymer container 202 and bioactive agent is placed in the bioactive agent container 204. Further, a mold (not shown), such as, for example, a mold similar to the mold embodiment described above, is positioned in the press 212, and the press 212 is actuated to retain the mold. The system 200 can then be actuated to use hydraulic pressure to push the polymer from the polymer container 202 along the line 208 into the mixer 206 and at the same time to push the bioactive agent from the bioactive agent container 204 along the line 210 into the mixer 206. The mixer 206 mixes the two components and the resulting mixture is pushed along the line 214 to the mold positioned in the press 212. The mixture is injected into the mold by forcing the mixture into the overmolding cavity (not shown) of the mold, as discussed above.

It is understood that any type of mold for use in such overmolding procedures could be used with the liquid injection system embodiments described herein.

The use of a liquid injection system 200 allows for a fast, efficient, consistent, and repeatable overmolding process that produces leads having one or more drug-eluting components with significantly reduced variation in dimensions and structure in comparison to drug-eluting components produced by prior art methods. It is understood that any known liquid injection system similar to the system 200 described above with respect to FIG. 6 could be used to produce the drug-eluting components described herein.

Alternatively, a transfer overmolding process can be utilized in which the mixture can be inserted into a mold via known methods using a transfer press. In this embodiment, the mold is positioned in the transfer press, and then the mixture is transferred from a mixer to a transfer apparatus. In this embodiment, the transfer apparatus is a syringe-like apparatus with a plunger. The transfer apparatus is then coupled to the mold and the mixture is injected into the mold.

In yet another alternative, one or more drug-eluting components can be placed on a lead body by any known injection or compression method. Further, any known method can be used for producing the drug-eluting components as described herein and placing them on a lead body.

Once the mixture has been injected into the mold, the lead and the drug-eluting component are allowed to cure before the lead with the component is removed from the mold. In this embodiment, the mold is heated to apply heat to the liquid mixture in the mold, which speeds up the curing process.

In one implementation utilizing a transfer molding process, the curing period in the heated mold can range from about 15 minutes to about 1 hour. In another transfer molding embodiment, the heat applied during the curing period can range from about 80° to about 200° C.

In another implementation utilizing a liquid injection molding process, the curing period can range from about 1 second to about 1 hour. Alternatively, the curing period can range from about 10 seconds to about 1 minute. In another liquid injection embodiment, the heat applied during the curing period can range from about 100° to about 200° C.

When the curing period is complete, the lead having at least one drug-eluting component can be removed from the mold.

In an alternative embodiment, the one or more drug-eluting components need not be overmolded onto the lead body. That is, the one or more drug-eluting components could instead be created by a molding process similar to that described above (without the overmolding step) in a process called "premolding" and then can be physically positioned on the lead body by any known application method.

As discussed above, according to various embodiments, in use, a drug-eluting lead can be delivered to a desired site within the patient's body. Once implanted, the bioactive agent may elute from the surface of the implant and diffuse into the adjoining tissue. In this manner, the inflammatory process and/or other unwanted biological processes associated with implantation and the presence of the foreign object can be suppressed (e.g., reduced inflammation and/or toxicity of inflammatory response). Alternatively, the growth of non-excitable, connective tissue around the electrode (e.g., the fibrotic capsule) can be reduced (e.g., a reduction in fibrotic capsule thickness may be observed), and thus, the postoperative rise in the stimulation threshold lessens, and a stable reduced threshold, both acute and chronic, is thereby provided. In yet another alternative, the drug-eluting devices disclosed herein can also facilitate extraction of the lead body due to lower fibrous capsule formation. Additionally, the device and methods may prevent myocyte cell function impairment and/or necrosis around, near or on an electrode, which may further stabilize a reduced threshold.

Various modifications and additions can be made to the exemplary embodiments discussed without departing from the scope of the present invention.

For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical lead, comprising:
   a lead body including a proximal end adapted to be coupled to a pulse generator and a distal region including a distal tip having an outer surface having a tapered cross-sectional profile extending from a proximal end of the distal tip to a distal end of the distal tip;
   a ring-shaped electrode located on the lead body proximal of the tapered cross-sectional profile of the distal tip;
   a recess formed in and extending along the outer surface of the distal tip;
   at least one conductor extending within the lead body from the proximal end to the ring-shaped electrode, the ring-shaped electrode operatively coupled to the at least one conductor; and
   a drug-eluting component disposed in the recess formed in the distal tip, wherein the drug-eluting component has a tapered cross-sectional profile corresponding to the tapered cross-sectional profile of the distal tip such that the tapered cross-sectional profile of the outer surface of the distal tip extends distally from the drug-eluting component.

2. The implantable lead of claim 1, wherein the tapered distal tip comprises silicone rubber.

3. The implantable lead of claim 1, wherein the drug-eluting component comprises dexamethasone acetate and silicone rubber.

4. The implantable lead of claim 1, wherein the drug-eluting component is an overmolded drug-eluting collar that encircles the tapered distal tip.

5. The implantable lead of claim 1, wherein an outer surface of the drug-eluting component is flush with the outer surface of the tapered distal tip from the proximal end to the distal end of the tapered distal tip such that the tapered profile of the distal tip is maintained.

6. The implantable lead of claim 1, wherein an outer surface of the drug-eluting component does not substantially protrude above the outer surface of the tapered distal tip, wherein a step tolerance between an outer surface of the drug-eluting collar and an outer surface of the distal tapered tip is less than about 0.005 inches.

7. The implantable lead of claim 1, wherein the recess is formed in the outer surface of the tapered distal tip such that it is located between a proximal and a distal end of the tapered distal tip.

8. An implantable medical lead, comprising:
   a lead body including a proximal end adapted to be coupled to a pulse generator and a distal region including a distal tip having an outer surface defining a tapered cross-sectional profile extending from a proximal end of the distal tip to a distal end of the distal tip and a recess formed in and extending along the outer surface of the distal tip such that the recess extends around an entire circumference of the tapered distal tip;
   a ring-shaped electrode located on the lead body proximal of the tapered cross-sectional profile of the distal tip; at least one conductor extending within the lead body from the proximal end to the ring-shaped electrode, the ring-shaped electrode operatively coupled to the at least one conductor; and
   a circumferential drug-eluting collar disposed in the recess formed in the distal tip, wherein the drug-eluting collar has a tapered cross-sectional profile corresponding to the tapered cross-sectional profile of the distal tip and extends around the entire circumference of the tapered distal tip, the tapered cross-sectional profile of the outer surface of the distal tip extending distally from the drug-eluting collar.

9. The implantable lead of claim 8, wherein the drug-eluting collar comprises dexamethasone acetate and silicone rubber.

10. The implantable lead of claim 8, wherein an outer surface of the drug-eluting collar is flush with the outer surface of the tapered distal tip from the proximal end to the distal end of the tapered distal tip such that the tapered profile of the distal tip is maintained.

11. The implantable lead of claim 8, wherein an outer surface of the drug collar does not substantially protrude above the outer surface of the tapered distal tip, wherein a step tolerance between an outer surface of the drug-eluting collar and an outer surface of the distal tapered tip is less than about 0.005 inches.

12. The implantable lead of claim 8, wherein the recess is formed in the tapered distal tip such that the recess is located between a proximal end and a distal end of the tapered distal tip.

* * * * *